United States Patent
Scialdone et al.

(10) Patent No.: US 9,085,747 B2
(45) Date of Patent: Jul. 21, 2015

(54) METHOD FOR THE ENHANCED RECOVERY OF CATMINT OIL

(75) Inventors: Mark A. Scialdone, West Grove, PA (US); David L. Hallahan, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 135 days.

(21) Appl. No.: 13/509,061

(22) PCT Filed: Nov. 10, 2010

(86) PCT No.: PCT/US2010/056167
§ 371 (c)(1),
(2), (4) Date: May 10, 2012

(87) PCT Pub. No.: WO2011/060027
PCT Pub. Date: May 19, 2011

(65) Prior Publication Data
US 2012/0238768 A1    Sep. 20, 2012

Related U.S. Application Data

(60) Provisional application No. 61/260,370, filed on Nov. 11, 2009.

(51) Int. Cl.
*A61K 36/53*    (2006.01)
*C11C 3/12*    (2006.01)

(52) U.S. Cl.
CPC ..................... *C11C 3/126* (2013.01)

(58) Field of Classification Search
USPC ......................................................... 424/725
IPC ........... A61K 36/53,2236/37, 2236/39, 2236/55
See application file for complete search history.

(56) References Cited

U.S. PATENT DOCUMENTS

| | | |
|---|---|---|
| 4,062,937 A | 12/1977 | Rea |
| 4,416,881 A | 11/1983 | McGovern |
| 4,496,467 A | 1/1985 | Munteanu |
| 4,869,896 A | 9/1989 | Coulston |
| 4,913,893 A | 4/1990 | Varco |
| 6,462,015 B1 | 10/2002 | Weiss |
| 6,524,605 B1 * | 2/2003 | Coats et al. ................... 424/408 |
| 6,673,756 B2 | 1/2004 | Sonnenberg |
| 7,067,677 B2 | 6/2006 | Manzer |
| 7,232,844 B2 | 6/2007 | Hallahan |
| 7,547,793 B2 * | 6/2009 | Hallahan et al. ............. 549/283 |
| 7,820,145 B2 | 10/2010 | Tamarkin |
| 2004/0024054 A1 | 2/2004 | Haenke |
| 2005/0112166 A1 | 5/2005 | Hallahan |
| 2005/0244441 A1 | 11/2005 | Courtois |
| 2006/0223878 A1 | 10/2006 | Scialdone |
| 2006/0240079 A1 * | 10/2006 | Hallahan et al. ............... 424/442 |
| 2007/0077262 A1 | 4/2007 | Scialdone |
| 2007/0264297 A1 | 11/2007 | Scialdone et al. |
| 2008/0305135 A1 | 12/2008 | Kroepke |
| 2010/0034906 A1 | 2/2010 | Gonzalez et al. |
| 2010/0092404 A1 | 4/2010 | Hutchenson |
| 2010/0145077 A1 | 6/2010 | Jackson |
| 2010/0145078 A1 | 6/2010 | Fisher |
| 2010/0168447 A1 | 7/2010 | Hutchenson et al. |
| 2010/0261915 A1 | 10/2010 | Gonzalez |

FOREIGN PATENT DOCUMENTS

| WO | 03/062357 | 7/2003 |
|---|---|---|
| WO | 2008/079261 | 7/2008 |

OTHER PUBLICATIONS

De Pooter et al. Flavour and Fragrance Journal. 1988. vol. 3, pp. 155-159.*
International Search Report PCT/US2010/056167, International Filing Dagte Nov. 10, 2010.
Regnier, Studies on the Composition of the Essential Oils of Three Nepeta Species, Phytochemistry, 1967, 6:1281-1289.
Baranauskiene, Sensory and Instrumental Evaluation of Catnip (*Nepeta cataria* L.) Aroma, 2003, 51, pp. 3840-3848.
Tanimori et. al., Total Synthesis of (+) Dihydronepetalactone, Agric. Biol. Chem., 1991, vol. 55:1181-11832.
T. Eisner, Science, 1964, vol. 146:1318-1320.
Wolinsky et. al., Syntheses of the Dihydronepetalactones, J. Org. Chem., 1972, vol. 37:3376-3378.
Jefson et. al., Chemical Defense of a Rove Bettle, Journal of Chemical Ecology, 1983, vol. 9:150-180.
G.W.K. Cavill et. al., Defensive and Other Secretions of the Australlian Cocktail Ant, Iridomyrmex Nitidiceps, Tetrahedron, 1982, vol. 38:1931-1938.
Nepetalactone and Epinepetalactone from Nepeta Cataria L.; F.E. Regnier et al; 6 Phytochemistry1271-1279, 1967; Pergamon Press, England.
(4aS,7S,7aR)-Nepetalactam and (4aS,7S,7aR)-2-[(3R,4R,4aR,7S,7aR)-Octahydro-4,7-dimethyl-1-oxocyclopental[c]pyran-3-yl]nepetalactam: Nitrogen analogues of Nepetalac Anhydride; Edmund J. Eisenbraun et al; 53 J. Org. Chem. 3968-3962, 1988; American Chemical Society, New York.

* cited by examiner

*Primary Examiner* — Chris R Tate

(57) ABSTRACT

A high yielding method is described for recovery of catmint oil from catmint plants of the genus *Nepeta* by improved separation of a catmint oil containing phase from the condensed steam distillate of catmint plants. Catmint oil may be obtained in quantitative yields for use in insect repellent compositions.

15 Claims, No Drawings

METHOD FOR THE ENHANCED RECOVERY OF CATMINT OIL

This application claims priority under 35 U.S.C. §119(e) from, and claims the benefit of, U.S. Provisional Application No. 61/260,370, filed Nov. 11, 2010, which is by this reference incorporated in its entirety as a part hereof for all purposes.

TECHNICAL FIELD

This invention provides methods for improved recovery of catmint oil from plants of the genus *Nepeta* (catmint).

BACKGROUND

It has been demonstrated that dihydronepetalactone exhibits insect repellency (see, for example, US 2005/0112166, which is by this reference incorporated in its entirety as a part hereof for all purposes). Dihydronepetalactone can be obtained by hydrogenation of nepetalactone, which may be isolated as a component of the essential oil of plants of the genus *Nepeta* (catmint plant). Essential oil from *Nepeta* plant material, herein referred to as catmint oil, has been obtained by various isolation processes, including steam distillation, organic solvent extraction, microwave-assisted organic solvent extraction, supercritical fluid extraction, mechanical extraction and enfleurage (initial cold extraction into fats followed by organic solvent extraction). Steam distillation [such as described by Regnier, F. E. et al, *Phytochemistry* (1967) 6:1281-1289] is the most viable method for obtaining catmint oil. Disclosed in a commonly owned and co-pending application published as US 2010/0034906 (which is by this reference incorporated in its entirety as a part hereof for all purposes) are improved processes for steam distilling plant material from *Nepeta cataria* to obtain catmint oil.

For commercial production of the insect repellent dihydronepetalactone as derived from catmint oil, it is desirable to have further increased yields of catmint oil containing nepetalactone obtained from *Nepeta* plant material. A need thus remains for improved techniques for the recovery of catmint oil from *Nepeta* plants.

SUMMARY

The invention provides methods for recovering catmint oil that increase the yield of catmint oil following steam extraction of catmint oil plants which are of the genus *Nepeta*.

Accordingly, this invention provides a method for recovering catmint oil from plants of the genus *Nepeta* by (a) contacting *Nepeta* plant material with steam to form a volatilized mixture comprising catmint oil and water; (b) condensing the volatilized mixture to form a first liquid mixture comprising catmint oil and water; (c) contacting the first liquid mixture with at least one non-water miscible organic extracting solvent to form a second liquid mixture that contains a solvent phase and an aqueous phase; (d) in the second liquid mixture, separating the solvent phase from the aqueous phase, and recovering the solvent phase; and (e) removing the extracting solvent from the solvent phase to isolate the catmint oil.

In another embodiment, this invention provides a method for recovering catmint oil from plants of the genus *Nepeta* by (a) contacting *Nepeta* plant material with steam to form a volatilized mixture comprising catmint oil and water; (b) condensing the volatilized mixture to form a first liquid mixture comprising catmint oil and water; (c) in the first liquid mixture, separating catmint oil from water, and recovering the catmint oil; (d) contacting the catmint oil recovered in (c) with at least one non-water miscible extracting solvent to form a second liquid mixture that contains a solvent phase and an aqueous phase; (e) in the second liquid mixture, separating the solvent phase from the aqueous phase, and recovering the solvent phase; and (f) removing the extracting solvent from the solvent phase to isolate the catmint oil.

In a further embodiment, the combination of the catmint oil obtained in steps (c) and (f) is the total isolated catmint oil.

In yet another embodiment, this invention provides a method for recovering catmint oil from plants of the genus *Nepeta* by (a) providing a first liquid mixture comprising catmint oil and water; (b) contacting the first liquid mixture with at least one non-water miscible organic extracting solvent to form a second liquid mixture that contains a solvent phase and an aqueous phase; (c) in the second liquid mixture, separating the solvent phase from the aqueous phase, and recovering the solvent phase; and (d) removing the extracting solvent from the solvent phase to isolate the catmint oil.

In yet another embodiment, this invention provides a method for recovering catmint oil from plants of the genus *Nepeta* by (a) providing a first liquid mixture comprising catmint oil and water; (b) in the first liquid mixture, separating catmint oil from water, and recovering the catmint oil; (c) contacting the catmint oil recovered in (b) with at least one non-water miscible extracting solvent to form a second liquid mixture that contains a solvent phase and an aqueous phase; (d) in the second liquid mixture, separating the solvent phase from the aqueous phase, and recovering the solvent phase; and (e) removing the extracting solvent from the solvent phase to isolate the catmint oil.

In yet another embodiment, the combination of the catmint oil obtained in steps (b) and (e) is the total isolated catmint oil.

DETAILED DESCRIPTION

This invention relates to improved methods for the recovery of catmint oil from plant material of the genus *Nepeta*. Catmint oil contains nepetalactone, and nepetalactone when hydrogenated yields dihydronepetalactone, which has been found to serve as an insect repellent active. The term "insect repellent" or "insect repellent composition", as used herein, refers to a compound or composition that deters insects from their preferred hosts or from articles of manufacture. Typically, an insect repellent is a compound or composition that can be either topically applied to a host, or incorporated into an article to deter insects from the space in which the host or article exists.

Improved Catmint Oil Extraction

Catmint oil exhibits several characteristics that lead to low recovery of the oil from plant material using standard steam distillation techniques commonly employed for the isolation of essential oils from plant material. Catmint oil has a similar density to water, and does not readily coalesce to form a separate oil phase from the condensed water used in the steam distillation process. Additionally, nepetalactone, the principal constituent of catmint oil, hydrates at high temperatures to non-volatile and unwanted side products. This invention overcomes these disadvantages of the isolation of catmint oil from plant material to provide an enhanced method for recovering the oil in high yield at moderate temperatures.

In the methods hereof, the volatized mixture of catmint oil and water solution resulting from steam distillation of *Nepeta* plant material (herein also called catmint plant material) is contacted with a non-water miscible organic solvent that dissolves catmint oil. Applicants have found that by using this extracting solvent, there is isolation of substantial amounts of catmint oil that remain in the aqueous portion of the steam distillate when a catmint oil phase is separated without using the extracting solvent. Removal of the solvent under reduced pressure affords catmint oil suitable for use in the preparation of hydrogenated catmint oil insect repellent. The yield of catmint oil may be improved by at least about 50%, 55%, 60%, 65%, 70%, or greater to achieve overall quantitative yields of at least about 80%, 85%, 90%, 95%, or 99%. For example, the yield of catmint oil may, by a factor as set forth above, be greater than the yield of catmint oil obtained from the separation of catmint oil from water in the absence of an organic extracting solvent. The amount of improvement in recovery will vary depending on factors including the level of recovery from steam distillation alone in a particular process, the organic solvent used for further extraction, and use of repetitions of an extraction process.

Steam Distillation

In the methods hereof, catmint oil plants are subjected to steam distillation with improved extraction following condensation of the resulting volatized mixture of catmint oil and water. Any plants of the genus *Nepeta* that contain nepetalactone in the catmint oil may be used. Preferred are plants of *Nepeta cataria*. Any method for steam distillation of plant material that is known in the art may be used such as that typically used for catmint oil recovery.

For example, according to conventional distillation processes for recovering catmint oil, plant material from *Nepeta cataria* is contacted with steam to form a vapor phase heterogeneous mixture comprising predominantly catmint oil and water. This volatized mixture is then condensed to form a heterogeneous liquid mixture comprising catmint oil and water.

Diagrams of typical distillation apparatuses are shown in commonly owned and co-pending application WO 2008/079261, which is by this reference incorporated in its entirety as a part hereof for all purposes. A traditional steam distillation apparatus may be used according to the following description. Plant material is packed into a retort over a set of steam injectors. A suitable retort that may be used for such purpose is available from Juniper Mfg. (Redmond, Oreg.). The lid of the retort is closed and sealed to both the retort and to a condenser. Steam is injected through the injection manifold (or steam injector) and into the packed plant material. The steam provides two functions: 1) energy to disrupt the glandular (or secretory) trichomes on the plant and release the oil, and 2) formation of a heteroazeotrope with the oil which volatizes it sufficiently as to allow it to be transported into the vapor phase. The steam and volatized oil are condensed as a mixture distillate.

Cooling water, from any suitable water source, flows through the condenser. Its cooling effect allows the steam and catmint oil vapor to condense. The condenser is configured in such a way as to allow gravity to drain the condensed water and catmint oil out of the condenser and into a collection can. The water and catmint oil are ducted into the collection can optionally using internal baffles in such a way as to produce a quiescent zone to allow the oil and water to effectively separate. The quiescent zone is the zone where the superficial velocity of the condensate is less than the disengagement velocity of the oil from the water. Typically, the temperature of the condensate is controlled at a modest temperature, approximately 40-60° C., to allow the oil and water to effectively separate in the quiescent zone of the separation can.

In known steam distillation processes for recovery of catmint oil, the separated catmint oil and water form two phases with the catmint oil being the heavier, lower layer. The water is generally removed as wastewater, for example by decantation.

In addition, the steam distillation may be carried out in a distillation apparatus as described below. Plant material is packed into a retort. The lid of the retort is closed and sealed to both the retort and to a condenser. Steam for the distillation of the catmint plant material can be provided by any suitable means such as by direct injection through an injection manifold. In an alternative embodiment, the steam can be obtained by adding water to the retort, and boiling the water in the presence of the plant material. The latter method is referred to as using a direct fired retort. The steam and volatized catmint oil are condensed, the catmint oil separated and collected as described above.

In one example of a steam extraction process, 13 kg of dried catmint plant material is packed into the retort above the steam injector so that the retort is full, and the plant material is sealed securely to the sides of the retort so that channeling of the steam along the inside walls of the retort is minimized. The retort is sealed and made leak tight. Live steam produced in a separate boiler is injected into the bottom of the retort at a rate of 480 g/min for a total of 60 minutes. The pressure of the steam is slightly above atmospheric pressure to allow for pressure drop across the plant material and the condenser. The cooling water flow is adjusted to the condenser so that the condensate temperature is between about 45° C. and about 55° C. during the distillation. It is desired to keep the temperature below about 75° C., and preferably below about 60° C. or about 55° C. to reduce the tendency for the hydration of nepetalactone to occur. Rate of hydration to nepetalic acid, an undesirable by-product, increases with increasing temperature. The temperature can be reduced by operating the distillation apparatus under vacuum.

The amount of vacuum applied to the system will depend on the system components, however achieving an absolute pressure of about 13 kPa to about 70 kPa is preferred. An absolute pressure of about 20 kPa to about 45 kPa is more preferred. In addition, the application of vacuum can be used in systems where water is recycled from the collection can back to the retort.

After the collection can is filled with condensate, the water phase condensate is drawn from the collection can into a wastewater drain, or the water is recycled. The still is operated in this fashion for 1 hour. A total of approximately 2.2 kg of steam is used per kg of dried catmint plant material. Approximately 50 mL or 52 grams of catmint oil is collected in the bottom of the collection can. This corresponds to approximately 0.40 wt % of the original dry weight of the catmint plant.

Enhanced Catmint Oil Recovery

In the methods hereof, recovery of catmint oil from the volatized-then-condensed mixture of catmint oil and water solution, obtained in a process as described above, is improved by enhancing separation of a catmint oil-containing phase (solvent phase) and the aqueous phase of the distillate mixture. At least one extraction solvent that is a non-water miscible organic solvent that dissolves catmint oil remaining with the aqueous phase is added to the condensed mixture of catmint oil and water solution. Extraction solvents that may be used are any organic solvents that are non-water miscible, that dissolve catmint oil in an aqueous mixture, and that provide increased disengagement of catmint oil from the aqueous portion of the mixture. Such extraction solvents will have a density that differs from water density in a greater amount than does the catmint oil density. Typically the density of the extraction solvent differs from that of water by at least about 0.1 g/cc. The difference may be either positive or negative.

Extraction solvents that may be used include without limitation hexanes, petroleum ether, toluene, xylenes, ethyl acetate, methyl acetate, dichloromethane (DCM) and chloroform. Due to the larger differences in densities and hydrophobicities of these solvents with respect to an aqueous solution, as compared to the density and hydrophobicity of catmint oil, the dissolved catmint oil in these solvents will more easily partition from the water in the condensed steam distillate into a separate layer that can then be isolated from the aqueous layer.

Typically a single extraction solvent is used, although multiple solvents may be used as mixtures or sequentially. Typically the extraction solvent is added to the condensed steam distillate and the combination mixed then allowed to separate. Mixing may be by any method such as by injection, stirring or shaking. Separation may be by any method such as settling or floating. Separation characteristics will depend on the specific extraction solvent used. For example, when using hexane as the extraction solvent, the separated hexane and catmint oil will float on the aqueous portion of the mixture. When using dichloromethane (DCM) as the extraction solvent, the separated DCM and catmint oil will, by contrast, settle below the aqueous portion of the mixture. Removal of the solvent under reduced pressure affords catmint oil suitable for use in the preparation of hydrogenated catmint oil insect repellent.

The placement of a line that directs water from the collection can to the retort will depend on the position of the water in the collection can, i.e. whether the water phase is on top of the catmint oil or below the catmint oil. Conventional collecting equipment may be used when the extraction solvent and catmint oil phase separates on top of the aqueous solution. In addition, corrosion products that may be formed in the condenser or collection can collect at the bottom of the collection can, contaminating the liquid phase that is at the bottom of the can. Therefore, an additional advantage to having the oil phase as the top phase is that it is separated from any corrosion products that may be present.

The extraction solvent and aqueous mixture may be collected into a collection can optionally using internal baffles in such a way as to produce a quiescent zone to allow the extraction solvent containing catmint oil phase and aqueous phase to effectively separate as described above for the original separation of catmint oil and aqueous mixture.

The extraction solvent containing catmint oil is isolated and the extraction solvent is removed by any suitable method known in the art such as by evaporation. The extracting solvent may be recovered and recycled.

In an alternative embodiment, extracting solvent is added to the aqueous phase following separation of a catmint oil phase from aqueous phase from the condensed steam extraction mixture with no extracting solvent added. In this embodiment a portion of catmint oil is isolated without using an extracting solvent, and an additional portion of catmint oil is recovered using an extracting solvent.

In another embodiment extraction with the extracting solvent is performed multiple times by addition to the initial condensed steam extraction mixture, and/or to the initial separated aqueous phase, and to subsequent separated aqueous phases. Extractions may be performed until at least about 50%, 55%, 60%, 65%, 70%, 75%, 80%, 85%, 90%, 95%, or 99% of catmint oil in the condensed steam distillate from catmint oil plant material is recovered.

Application of Catmint Oil

Recovered catmint oil may be used to prepare an insect repellent composition. The catmint oil is hydrogenated to convert the nepetalactone into dihydronepetalactone, which is an effective insect repellent. Nepetalactone, which naturally occurs in different stereoisomers in catmint oil, is hydrogenated to form mixtures of dihydronepetalactone stereoisomers, or dihydronepetalactones. One example of hydrogenation to produce dihydronepetalactones using catalysts such as palladium, or carbon and palladium, supported on strontium carbonate is described in Regnier et al [*Phytochemistry* 6:1281-1289 (1967)].

For example, the hydrogenation reaction may be carried out in the presence of hydrogen at a temperature of about −10° C. to about 200° C. The hydrogen pressure for the reaction is generally from about 0.1 MPa to about 20.7 MPa. The time, temperature, hydrogen pressure and flow rate and feed may be adjusted, according to known principles, to obtain optimal conversion of hydrogenation of catmint oil using a given catalyst. A suitable hydrogenation reaction is that which is described in U.S. Pat. No. 7,067,677 (which is by this reference incorporated in its entirety as a part hereof for all purposes). Described therein is the hydrogenation of nepetalactone in the presence of a catalytic metal that is not nickel, platinum or palladium. The process can be carried out at a temperature of about 25° C. to about 250° C. at a hydrogen pressure of about 0.1 MPa to about 20 MPa. Other suitable processes for making a dihydronepetalactone include a process as described in the commonly owned and co-pending application published in U.S. 2010/0168447, which is by this reference incorporated in its entirety as a part hereof for all purposes. A hydrogenation reaction may be carried out in batch in a single reactor, in sequential batch in a series of reactors, in reaction zones within one or more reactors, or in continuous mode in any of the equipment customarily employed for continuous processes.

Hydrogenated catmint oil is incorporated into formulations suitable for application to the skin, hair, fur, feathers or hide of a human or domesticated animal. In addition, insect repellent formulations may be applied to, or incorporated into articles. Insect repellent formulations are designed to provide a minimum effective evaporation rate from the skin surface or insect repellent article to maintain the necessary minimum concentration of repellent in the air space directly above the skin surface/article for effective insect repellency. Disclosed in commonly owned and co-pending applications published, respectively, as US 2005/112166 and US 2007/0264297 (each of which is by this reference incorporated in its entirety as a part hereof for all purposes) are effective carriers and insect repellent compositions prepared using catmint oil.

Insect repellent compositions containing dihydronepetalactones are effective against a variety of insects which interfere with human society including a variety of biting insects (ants, bees, black flies, chiggers, fleas, mosquitoes, stable flies, ticks, wasps), wood-boring insects (termites), noxious insects (house flies, cockroaches, lice, wood lice), and household pests (flour and bean beetles, dust mites, moths, silverfish, weevils).

EXAMPLES

The operation and effects of certain embodiments of the inventions hereof may be more fully appreciated from a series of examples (Examples 1~2), as described below. The embodiments on which these examples are based are representative only, and the selection of those embodiments to illustrate the invention does not indicate that materials, components, reactants, conditions, steps or techniques not described in the examples are not suitable for use herein, or that subject matter not described in the examples is excluded from the scope of the appended claims and equivalents thereof.

The following abbreviations are used: ° C. is degrees Centigrade; Kg is kilogram; g is gram; min is minute; ml is milliliter(s); CMO is catmint oil.

Example 1

Extraction of Catmint Oil from CMO/Water Mixture with Dichloromethane

Catmint oil (purchased from Thacker brothers, 1.73 g) was added to a separatory funnel followed by addition of 100 g of water. The mixture (approximately 1.73% weight/weight) was stirred, and the catmint oil (CMO) layer, which is slightly heavier than water, was allowed to settle. The CMO layer was then separated from the water layer in a separatory funnel and weighed. This recovered CMO was called the first amount of CMO.

Droplets of CMO remaining in the water layer were visible indicating that the CMO did not fully separate from the water. A volume of 20 ml dichloromethane (DCM), a solvent heavier than water, was then added to the separatory funnel containing rest of the CMO/water mixture. The funnel was shaken. Droplets of CMO disappeared when DCM was added, and the CMO/water mixture was shaken indicating that the CMO partitioned into the DCM fraction. The DCM, including partitioned CMO, was allowed to settle and then was isolated from the separatory funnel. A total of three extractions were performed using 20 ml DCM each time, and the three CMO/DCM mixtures were combined. The combined CMO/DCM mixtures were dried over sodium sulfate, and DCM was removed under reduced pressure on a rotary evaporator. The resulting sample, which was the second amount of CMO, was weighed. Together the first and second amounts of CMO gave the total CMO yield. Total percent CMO yield was calculated by dividing the total weight of CMO recovered in grams as a fraction of starting CMO amount (1.73 g). Results are given in Table 1 below.

Example 2

Extraction of Catmint Oil from CMO/Water Mixture with Hexane

Catmint oil (purchased from Thacker brothers, 1.56 g) was added to a separating funnel followed by addition of 150 g of water. The mixture (approximately 1.04% weight/weight) was stirred, and the catmint oil (CMO) layer, which is slightly heavier than water, was allowed to settle. The CMO layer was then separated from the water layer and weighed. This recovered CMO was called the first amount of CMO.

Droplets of CMO remaining in the water layer were visible indicating that the CMO did not fully separate from the water. A volume of 20 ml hexane (HXN), a solvent lighter than water, was then added to the separatory funnel containing the rest of the CMO/water mixture. The funnel was shaken. Droplets of CMO disappeared when HXN was added, and the CMO/water mixture was shaken indicating that the CMO partitioned into the HXN fraction. The HXN, including partitioned CMO, was allowed to float and then was isolated from the separatory funnel. A total of three extractions were performed using 20 ml HXN each time, and the three CMO/HXN mixtures were combined. The combined CMO/HXN mixtures were dried over sodium sulfate, and HXN was removed under reduced pressure on a rotary evaporator. The resulting sample, which was the second amount of CMO, was weighed. Together the first and second amounts of CMO gave the total CMO yield. Total percent CMO yield was calculated by dividing the total weight of CMO recovered in grams as a fraction of starting CMO amount (1.56 g). Results are given in Table 1.

TABLE 1

Recovery of CMO from water.

| Starting CMO (g) | Water (g) | Solvent | Starting CMO % in water | First amount of CMO (g) | % CMO recovered | Second amount of CMO (g) | Total CMO yield (g) | Total % CMO yield |
| --- | --- | --- | --- | --- | --- | --- | --- | --- |
| 1.73 | 100 | DCM | 1.73% | 0.45 | 26.01% | 1.27 | 1.72 | 99.42% |
| 1.56 | 150 | HXN | 1.04% | 0.34 | 21.79% | 0.97 | 1.31 | 83.97% |

In other embodiments, the methods hereof could be conducted as described below. Steam distillation of catmint oil is carried out in a distillation apparatus consisting of a retort, steam generator, condenser and receiver to capture the condensate. Dried catmint plant material is packed into the retort of the distillation apparatus so that the retort is full. The retort is sealed, and steam is injected into the bottom of the retort. The pressure of the steam is slightly above atmospheric pressure, and the cooling water temperature in the condenser of the distillation apparatus is adjusted so that the condensate temperature in the receiver is between 45° C. and 55° C. during the distillation.

After the distillation is complete, the collected condensate in the receiver mixture consisting of catmint oil and water is transferred to a separatory funnel. A water immiscible extraction solvent, such as hexane, is added and the mixture is shaken in order to thoroughly mix the water and solvent layers. The mixture is allowed to stand in order for the layers to completely separate into two distinct liquid phases. The water layer is separated from the extraction solvent layer. The extraction solvent is evaporated from the solvent layer for recovery of the catmint oil.

In yet another embodiment, the invention provides a process for recovering catmint oil from plants of the genus *Nepeta* comprising:
(a) contacting *Nepeta* plant material with steam to form a volatilized mixture comprising catmint oil and water;
(b) condensing the volatilized mixture of step (a) to form a first liquid mixture comprising catmint oil and water;
(c) contacting the first liquid mixture of (c) with at least one non-water miscible organic extracting solvent forming a second liquid mixture;

(d) separating a phase comprising catmint oil and the extracting solvent of (c) from an aqueous phase in the second liquid mixture of (c);
(e) recovering the catmint oil and extracting solvent phase of (d); and
(g) removing the extracting solvent from the catmint oil and extracting solvent phase of (e) to isolate the catmint oil.

In yet another embodiment the invention provides a process for recovering catmint oil from plants of the genus *Nepeta* comprising:
(a) contacting *Nepeta* plant material with steam to form a volatilized mixture comprising catmint oil and water;
(b) condensing the volatilized mixture of step (a) to form a first liquid mixture comprising catmint oil and water;
(c) separating a catmint oil phase from an aqueous phase in the first liquid mixture of (b);
(d) recovering the catmint oil phase of (c);
(d) contacting the aqueous phase of (c) with at least one non-water miscible extracting solvent forming a second liquid mixture;
(e) separating a phase comprising catmint oil and the extracting solvent of (d) from an aqueous phase in the second liquid mixture of (b);
(f) recovering the catmint oil and organic solvent phase of (e); and
(g) removing the extracting solvent from the catmint oil and organic solvent phase of (f) to isolate the catmint oil;
wherein the combination of the catmint oil of steps (c) and (g) is the total isolated catmint oil.

In yet another embodiment the invention provides a process for recovering catmint oil from plants of the genus *Nepeta* comprising:
(a) contacting *Nepeta* plant material with steam to form a volatilized mixture comprising catmint oil and water;
(b) condensing the volatilized mixture obtained in step (a) to form a first liquid mixture comprising catmint oil and water;
(c) contacting the first liquid mixture with at least one non-water miscible organic extracting solvent to form a second liquid mixture;
(d) separating from an aqueous phase in the second liquid mixture a solvent phase that comprises catmint oil and the extracting solvent; and
(e) removing the extracting solvent from the solvent phase to isolate catmint oil.

In yet another embodiment the invention provides a process for recovering catmint oil from plants of the genus *Nepeta* comprising:
(a) contacting *Nepeta* plant material with steam to form a volatilized mixture comprising catmint oil and water;
(b) condensing the volatilized mixture obtained in step (a) to form a first liquid mixture comprising catmint oil and water;
(c) separating catmint oil from an aqueous phase in the first liquid mixture;
(d) contacting the aqueous phase with at least one non-water miscible extracting solvent to form a second liquid mixture;
(e) separating from an aqueous phase in the second liquid mixture a solvent phase that comprises catmint oil and the extracting solvent; and
(f) removing the extracting solvent from the solvent phase to isolate catmint oil.

In yet another embodiment the invention provides a process for recovering catmint oil from plants of the genus *Nepeta* comprising:
(a) providing a first liquid mixture comprising catmint oil and water;
(b) contacting the first liquid mixture with at least one non-water miscible organic extracting solvent to form a second liquid mixture;
(c) separating from an aqueous phase in the second liquid mixture a solvent phase that comprises catmint oil and the extracting solvent; and
(d) removing the extracting solvent from the solvent phase to isolate catmint oil.

In yet another embodiment the invention provides a process for recovering catmint oil from plants of the genus *Nepeta* comprising:
(a) providing a first liquid mixture comprising catmint oil and water;
(b) separating catmint oil from an aqueous phase in the first liquid mixture;
(c) contacting the aqueous phase with at least one non-water miscible extracting solvent to form a second liquid mixture;
(d) separating from an aqueous phase in the second liquid mixture a solvent phase that comprises catmint oil and the extracting solvent; and
(e) removing the extracting solvent from the solvent phase to isolate catmint oil.

The term "invention" as used herein is a non-limiting term, and is not intended to refer to any single embodiment of the various inventions hereof to the exclusion of others, but encompasses all possible embodiments as described in the specification and the claims.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

What is claimed is:

1. A method for recovering catmint oil from plants of the genus *Nepeta*, comprising
   (a) contacting *Nepeta* plant material with steam to form a volatilized mixture comprising catmint oil and water;
   (b) condensing the volatilized mixture to form a first liquid mixture comprising catmint oil and water;
   (c) contacting the first liquid mixture with at least one first non-water miscible organic extracting solvent to form a second liquid mixture that contains a first solvent phase and a first aqueous phase;
   (d) in the second liquid mixture, separating the first solvent phase from the first aqueous phase, and recovering the first solvent phase;
   (e) removing the first extracting solvent from the first solvent phase to isolate catmint oil and provide a first isolated portion of catmint oil;
   (f) contacting the first aqueous phase with at least one second non-water miscible organic extracting solvent to form a third liquid mixture that contains a second solvent phase and a second aqueous phase;
   (g) in the third liquid mixture, separating the second solvent phase from the second aqueous phase, and recovering the second solvent phase;
   (h) removing the second extracting solvent from the second solvent phase to isolate catmint oil and provide a second isolated portion of catmint oil;
   wherein the first and second extracting solvents are the same or different; and
   wherein the first and second portions of isolated catmint oil are, optionally, combined.

2. A method for recovering catmint oil from plants of the genus *Nepeta*, comprising
   (a) contacting *Nepeta* plant material with steam to form a volatilized mixture comprising catmint oil and water;
   (b) condensing the volatilized mixture to form a first liquid mixture comprising catmint oil and water;
   (c) in the first liquid mixture, separating catmint oil from water, and recovering the catmint oil;
   (d) contacting the catmint oil recovered in (c) with at least one first non-water miscible extracting solvent to form a second liquid mixture that contains a first solvent phase and a first aqueous phase;
   (e) in the second liquid mixture, separating the first solvent phase from the first aqueous phase, and recovering the first solvent phase;
   (f) removing the first extracting solvent from the first solvent phase to isolate catmint oil and provide a first portion of isolated catmint oil;
   (g) contacting the first aqueous phase with at least one second non-water miscible organic extracting solvent to form a third liquid mixture that contains a second solvent phase and a second aqueous phase;
   (g) in the third liquid mixture, separating the second solvent phase from the second aqueous phase, and recovering the second solvent phase;
   (h) removing the second extracting solvent from the second solvent phase to isolate catmint oil and provide a second isolated portion of catmint oil;
   wherein the first and second extracting solvents are the same or different; and
   wherein the first and second portions of isolated catmint oil are, optionally, combined.

3. A method according to claim 1 or 2 wherein the yield of catmint oil is at least about 50% greater than the yield of catmint oil obtained from the separation of catmint oil from water in the absence of an organic extracting solvent.

4. A method according to claim 1 or 2 wherein the first and/or second water immiscible organic extracting solvent has a density that is different from the density of water by at least about 0.1 g/cc.

5. A method according to claim 4 wherein the first and/or second water immiscible organic extracting solvent is selected from the group consisting of a hexane, petroleum ether, toluene, a xylene, ethyl acetate, dichloromethane (DCM), chloroform and mixtures thereof.

6. A method according to claim 1 or 2 further comprising a step of hydrogenating isolated catmint oil.

7. A method according to claim 6 further comprising a step of formulating the hydrogenated catmint oil in an insect repellent composition.

8. A method according to claim 1 or 2 wherein *Nepeta* plant material is contacted with steam at an absolute pressure of about 13 kPa to about 70 kPa.

9. A method according to claim 8 wherein *Nepeta* plant material is contacted with steam at an absolute pressure of about 20 kPa to about 45 kPa.

10. A method according to claim 1 or 2 wherein the first liquid mixture is maintained at a temperature of below about 75° C.

11. A method according to claim 10 wherein the first liquid mixture is maintained at a temperature in the range of about 45° C. to about 55° C.

12. A method according to claim 1 or 2 wherein the first and/or second water immiscible organic extracting solvent has a density that is less than the density of water by at least about 0.1 g/cc.

13. A method according to claim 12 wherein the first and/or second water immiscible organic extracting solvent is selected from the group consisting of a hexane, petroleum ether, toluene, a xylene, ethyl acetate, and mixtures thereof.

14. A method according to claim 1 wherein, in the second liquid mixture and/or in the third liquid mixture, the solvent phase floats on top of the aqueous phase.

15. A method according to claim 2 wherein, in the second liquid mixture and/or in the third liquid mixture, the solvent phase floats on top of the aqueous phase.

* * * * *